United States Patent [19]  [11]  4,430,430
Momose et al.  [45]  Feb. 7, 1984

[54] METHOD FOR PRODUCING L-ARGININE BY FERMENTATION

[75] Inventors: Haruo Momose, Kamakura; Masaaki Ishida, Kawasaki; Mahito Terabe, Yokohama, all of Japan

[73] Assignee: Ajinomoto Co., Inc., Tokyo, Japan

[21] Appl. No.: 272,286

[22] Filed: Jun. 10, 1981

[30] Foreign Application Priority Data

Jun. 13, 1980 [JP] Japan .................................. 55-79959

[51] Int. Cl.³ .................. C12P 13/10; C12N 1/20; C12R 1/19
[52] U.S. Cl. .................................. 435/114; 435/253; 435/849; 435/317
[58] Field of Search ............... 435/114, 172, 317, 849, 435/253

[56] References Cited

U.S. PATENT DOCUMENTS 4,086,137  4/1978  Nakayama et al. ................ 435/172
4,278,765  7/1981  Debabor et al. ................... 435/172

OTHER PUBLICATIONS

Bachmann Recalibrated Linkage Map of *Ecoli* K-12 *Bateriological Reviews* Mar. 1976, p. 116-167.
Chakrabanty, *Genetic Engineering* C.R.C. Press, Inc., Palm Beach, 1978, pp. 101 and 105.

*Primary Examiner*—Albert T. Meyers
*Assistant Examiner*—Kathleen S. McCowin
*Attorney, Agent, or Firm*—Oblon, Fisher, Spivak, McClelland & Maier

[57] ABSTRACT

An L-arginine producing microorganism which is constructed by transforming into a recipient strain of the genus Escherichia of a vector having inserted therein an arg A gene derived from a chromosomal DNA of the genus Escherichia, is useful for the production of high levels of L-arginine by fermentation.

5 Claims, No Drawings

METHOD FOR PRODUCING L-ARGININE BY FERMENTATION

BACKGROUND OF THE INVENTION

1. Field of the Invention

The present invention relates to a method for producing L-arginine by fermentation:

2. Description of the Prior Art

Most of wild strains of microorganisms do not produce L-arginine in the medium. In order to render a wild strain capable of producing L-arginine from carbohydrates, it has been necessary to induce artificial mutants from the wild strain. There are many known arginine-producing artificial mutants. The most typical known arginine-producing mutants are as follows:

Mutants resistant to 2-thiazolealanine of the genus Brevibacterium or Corynebacterium (U.S. Pat. No. 3,723,249 and U.S. Pat. No. 3,878,044), mutant resistant to canavanine of the genus Corynebacterium (U.K. Pat. No. 1,351,518) mutant resistant to arginine-hydroxamate of the genus Bacillus (U.S. Pat. No. 3,734,829), and mutant resistant to canavanine of the genus Escherichia (Japanese Published Examined Patent Application No. 38115/1977).

It has however, become difficult to increase the yields of L-arginine by using the artificial mutation techniques. Therefore, a continuous need exists for the development of novel method for producing L-arginine in high yields.

SUMMARY OF THE INVENTION

It is therefore an object of the invention to provide a method for producing L-arginine in high yields.

This and other objects of the invention, which will hereinafter become more readily apparent, have been attained by providing a method, which comprises culturing an L-arginine producing microorganism of the genus Escherichia in a culture medium, and recovering the L-arginine accumulated in the culture medium, said L-arginine producing microorganism being incorporated with a vector DNA having inserted therein an arg A gene obtained from a chromosomal DNA of the genus Escherichia.

DETAILED DESCRIPTION OF THE PREFERRED EMBODIMENTS

Arg A gene, which controls synthesis of N-acetylglutamate (Bacteriological Reviews, vol 40, 116–167, March, 1976), is obtained from a DNA donor strain of the genus Escherichia having arg A gene. Desirable DNA donor strain has high enzyme activity of N-acetylglutamate synthesis, and/or has N-acetylglutamate synthetase less inhibited by L-arginine. Such desirable DNA donor strains usually have high productivity of L-arginine, and can be obtained as mutants resistant to α-methylmethionine, p-fluorophenylalanine, D-arginine, arginine hydroxamic acid, S-(2-aminoethyl)-cysteine, α-methylserine, β-2-thienylalanine, sulfaguanidine or canavanine. Chromosomal DNA is extracted from the DNA donor strain by a conventional manner. The vector DNAs may be E. coli plasmids or phages capable of replicating in E. coli. Among useful plasmids, the following can be listed: Col E1, pSC 101, RSF 2124, pMB8, pMB9, pACYC 177, pCK1, R6K, λ phage, pBR 312, pBR 313, pBR 317, pBR 318, pBR 320, pBR 321, pBR 322, pBR 333, pBR 341, pBR 345, pBR 350, pBR 351, pML 2, pML 21, Col E1Ap, RSF 1010, pVH 151, pVH 153 (Recombinant Molecules: Impact on Science and Society: Beers, R. F., and Bassett, E. G. eds., Raven Press, New York (1977)). Other plasmids are pBR 327, pBR 325 and pBR 328 (Soberon, et al, Gene 9: 287–305 (1980)); still others are described in "DNA Insertion Elements, Plasmids and Episomes", Bukhari et al (eds), Cold Spring Harbor Laboratory (1977). A preferred plasmid is pBR 322.

The chromosomal and vector DNAs are treated with a restriction endonuclease by a well known method (Biochem. Biophys. Acta 383: 457 (1975)). Various kinds of restriction endonuclease can be used, if the digestion of the chromosomal DNA is done partially. Thereafter, the digested chromosomal and vector DNAs are subjected to a ligation reaction.

Recipient strains for the hybrid DNA belong to the genus Escherichia. Although any kinds of Escherichia strains can be used as the recipient, it is convenient to use L-arginine requiring (especially arg A gene-deficient) mutant for the selection of strains transformed to L-arginine producers. Desirable results will be obtained when strains having high productivity of L-arginine are used as the recipients. Such high arginine producers do not require L-arginine for growth, are generally resistant to the above-mentioned drugs and/or are arg R deficient mutant. Naturally, decomposing activity of L-arginine of the recipient should be low.

It is more desirable that the hybrid DNA is inserted additionally with arg B gene, arg C gene, arg D gene, arg E gene, arg F gene, arg G gene, arg H gene and/or arg I gene (arg B,C, D,E,F,G,H and I genes are referred to in Bacteriological Reviews, vol 40, 116–167, March, 1976).

The methods of culturing the L-arginine producing strains thus obtained are conventional, and are similar to the methods for the cultivation of known L-arginine producing microorganisms. Thus, the culture medium employed is a conventional one containing carbon sources, nitrogen sources, inorganic ions and, when required, minor organic nutrients such as vitamins or amino acids. Examples of suitable carbon sources include glucose, sucrose, lactose, starch hydrolysate, molasses and whey, gaseous ammonia, aqueous ammonia and ammonium salts and other nitrogen containing materials can be used as the nitrogen source.

The cultivation of the recombinant microorganisms is conducted under aerobic conditions in which the pH and the temperature of the medium are adjusted to a suitable level and continued until the formation of L-arginine ceases.

The L-arginine accumulated in the culture medium can be recovered by conventional procedures.

By the method of the present invention, L-arginine can be produced in higher yields than has been achieved in previously known methods in which artificial mutants of Escherichia are used. Additionally by-produced amino acids are scarce and recovery of L-arginine can be carried out by a simple procedure.

Having generally described this invention, a further understanding can be obtained by reference to certain specific examples which are provided herein for purposes of illustration only and are not intended to be limiting unless otherwise specified.

EXAMPLE 1

(1) Preparation of chromosomal DNA possesing arg A gene

*Escherichia coli* AJ 11534 (NRRL B-12424) a mutant derived from K-12 (ATCC 10798), resistant to L-arginine-hydroxamate and deficient in arg R gene was cultured at 37° C. for 3 hours with shaking in 1 l of L-medium containing 1 g/dl peptone, 0.5 g/dl yeast extract, 0.1 g/dl glucose and 0.5 g/dl NaCl (pH was adjusted to 7.2), and bacterial cells in the exponential growth phase were harvested. Chromosomal DNA was extracted by a conventional phenol-method, and 4.8 mg of purified DNA was obtained.

(2) Preparation of vector DNA

As the vector, DNA of pBR 322 was prepared as follows:

A strain of *Escherichia coli* K-12 harboring the plasmid pBR 322 was incubated at 37° C. in 1 l of a medium containing: 2 g glucose, 1 g NH$_4$Cl, 6 g Na$_2$HPO$_4$, 3 g KH$_2$PO$_4$, 5 g NaCl, 0.1 g MgSO$_4$.7H$_2$O, 0.015 g CaCl$_2$.2H$_2$O, 20 g "casamino acid" (casein hydrolysate), 0.05 g thymine, 0.05 g L-tryptophan and 1000 μg thiamine.HCl per liter (pH was adjusted to 7.2). After the strain had been incubated until the late log phase, 170 μg/ml of chloramphenicol was added to the culture medium. The cultivation continued for 16 hours after the addition of chloramphenicol.

Cells were harvested and then lysed by treatment with lysozyme and sodium dodecylsulfate. The lysate was centrifuged at 30,000xg for one hour to obtain the supernatant. After concentrating the supernatant, 490 μg of plasmid pBR 322 DNA was obtained by fractionation using cesium chloride ethidium bromide equibrium density gradient centifugation.

(3) Insertion of chromosomal DNA fragment into vector

Thirty μg of the chromosomal DNA was treated with the restriction endonuclease Eco RI, Hind III, Bam HI, or Sal I at 37° C. for 15, 30, 60 or 120 minutes to cleave the DNA chains, and then heated at 65° C. for 5 minutes, respectively. Vector DNA was also treated with each of the restriction endonucleases mentioned above at 37° C. for 120 minutes to cleave the DNA completely, and then heated at 65° C. for 5 minutes.

The digested chromosomal DNA solution and cleaved vector DNA solution were mixed and subjected to the ligation reaction of DNA fragments by a T$_4$ phage DNA-ligase in the presence of ATP and dithiothreitol at 10° C. for 24 hours. The reaction mixture was then heated at 65° C. for 5 minutes, and two folds volume of ethanol was added to it. The precipitated recombinant DNA was recovered.

(4) Genetic transformation with the hybrid plasmid harboring arg A gene

As the recipient for the hybrid plasmid, an arginine auxotroph of which N-acetylglutamate synthetase, the product of arg A gene, had been inactivated (arg A$^-$). Since arg A gene is near to lys A gene (controlling lysine synthesis) on the chromosomal gene map, arg A deficient strain was selected from arginine requiring mutants as that arg A and lys A genes were co-transduced by P1 phage.

The arg A deficient mutant No. 13 (NRRL B-12425) thus obtained was inoculated in 10 ml of L-medium, and cultured at 37° C. with shaking.

Cells in exponential growth phase were harvested, and suspended in 0.1 M MgCl$_2$ solution and then in 0.1 M CaCl$_2$ solution in an ice-bath, whereby "competent" cells having the ability of DNA uptake were prepared.

Into the competent cell suspension, the DNA obtained in step (3), which contains the hybrid plasmid DNA, was added. The suspension was kept in an ice-bath for 30 minutes, then heated at 42° C. for 2 minutes, and again allowed to stand in an ice-bath for 30 minutes, the cells, thus being incorporated with the hybrid plasmid DNA, were inoculated into L-medium and the medium was shaken at 37° C. for 3 hours, whereby the transformation reaction was completed. The cells were harvested, washed, and resuspended. A small portion of the cell suspension was spread on an agar plate containing 2 g glucose, 1 g (NH$_4$)$_2$SO$_4$, 7 g K$_2$HPO$_4$, 2 g KH$_2$PO$_4$, 0.1 g MgSO$_4$.7H$_2$O, 0.5 g sodium citrate.2-H$_2$O, and 20 g agar, per liter (pH was adjusted to 7.2). The plate was incubated at 37° C. for 3 days.

Colonies appreared on the plate were picked up and purified. The purified strains were tested their resistance to ampicillin using L-medium further added with 20 μg/ml ampicillin. Thereafter, the arginine non-requiring and ampicillin resistant seventeen strains were tested for their productivity of arginine, and it was found that all seventeen strains produced L-arginine in the culture medium. This means that arg A gene of chromosomal DNA had been incorporated into pBR 322 plasmid, and the strains trasformed with the hybrid plasmid have excessive productivity of L-arginine. The most efficient arginine producer AJ 11593 (FERM-P 5616) (NRRL B-12426) was selected from the seventeen strains.

(5) Production of L-arginine by the novel L-arginine producing strains

Table 1 shows the experimental result of the fermentative production of L-arginine by using AJ 11593.

The fermentation medium contained 5 g/dl glucose, 2.5 g/dl ammonium sulfate, 0.2 g KH$_2$PO$_4$, 0.1 g/dl MgSO$_4$.7H$_2$O, 0.5 g/dl yeast extract, 100 μg/dl thiamine.HCl, 1 mg/dl FeSO$_4$.7H$_2$O, 1 mg/dl MnSO$_4$.4H$_2$O and 2.5 g/dl CaCO$_3$ (separately sterifized) and the pH was adjusted to 7.0.

Twenty ml bathces of the fermentation medium were placed in 500 ml flasks, inoculated with one loopful inoculum of the test microorganism, and the cultivation was carried out at 30° C. for 3 days.

The amount of arginine in the supernatant of the fermentation broth was determined by microbiological assay. The result is shown in Table 1-A.

EXAMPLE 2

The hybrid plasmid in AJ 11593 was separated by the manner in step (2) of Example 1, incorporated into AJ 11534 (which is arginine-non-requiring, arg R deficient and L-arginine-hydroxamate resistant) by the manner shown in step (4) of Example 1. Since arg A maker of recipient could not be used in this procedure, the maker of pBR 322 (ampicillin resistance) was used, and transformants grown on L-medium containing 20 μg/ml ampicillin were obtained.

Arginine producing AJ 11594 (FERM-P 5617) (NRRL B-12427) thus obtained was cultured by the method shown in step (5) of Example 1 to test the productivity of L-arginine. The result is shown in Table 1-B.

For the comparison, AJ 11534 was cultured by the same manner as above, and the result is shown in Table 1-C.

The molecular weight of the hybrid plasmid was 3.7 megadalton, and the moleculare weight of the inserted arg A gene was 1.1 megadalton, since pBR 322 is 2.6 megadalton.

TABLE 1

| | Test of L-arginine productivity | |
|---|---|---|
| | Strain tested | L-Arginine produced (mg/dl) |
| A | AJ 11593 | 6 |
| B | AJ 11594 | 190 |
| C | AJ 11534 | 75 |

What is claimed is:

1. A method for producing L-arginine by fermentation which comprises culturing in a culture medium an L-arginine producing microorganism selected from the group consisting of transformat NRRL B-12426 and transformat NRRL B-12427.

2. The method according to claim 1 wherein the L-arginine producing microorganism is the transformant NRRL B-12426.

3. The method according to claim 1, wherein the L-arginine producing microorganism is the transformant NRRL B-12427.

4. An L-arginine producing transformant of the genus Escherichia having the designation NRRL B-12426.

5. An L-arginine producing transformant of the genus Escherichia having the designation NRRL B-12427.

* * * * *